United States Patent [19]

McAleer et al.

[11] 4,039,657
[45] Aug. 2, 1977

[54] SEPARATING ANTIGEN FROM RESIDUAL COMMON SENSITIZING PROTEIN

[75] Inventors: William J. McAleer, Ambler; Edward H. Wasmuth, Telford, both of Pa.

[73] Assignee: Merck & Co., Inc., Rahway, N.J.

[21] Appl. No.: 676,265

[22] Filed: Apr. 12, 1976

Related U.S. Application Data

[63] Continuation-in-part of Ser. No. 588,270, June 19, 1975, abandoned.

[51] Int. Cl.$^2$ .................. A61K 39/12; A61K 39/20; A61K 39/00
[52] U.S. Cl. ........................................ 424/89; 424/88; 424/92
[58] Field of Search ............................ 424/88, 89, 92

[56] References Cited

U.S. PATENT DOCUMENTS

| | | | |
|---|---|---|---|
| 2,118,117 | 5/1938 | Sevag | 424/88 |
| 2,506,345 | 5/1950 | Cox et al. | 424/88 |
| 3,078,215 | 2/1963 | Fantes et al. | 424/89 |
| 3,316,153 | 4/1967 | Frank | 424/89 |

*Primary Examiner*—Sam Rosen
*Attorney, Agent, or Firm*—Donald J. Perrella; J. Jerome Behan

[57] ABSTRACT

Sensitizing plasma protein is dissociated from antigen-plasma protein complex by agitating at low temperature under controlled pH.

9 Claims, No Drawings

SEPARATING ANTIGEN FROM RESIDUAL COMMON SENSITIZING PROTEIN

RELATED APPLICATIONS

This application is a continuation-in-part of copending application Ser. No. 588,270, filed 19 June 1975, now abandoned.

SUMMARY OF THE INVENTION

A process for separating biological antigen having a particle size of from about 10 nm to about 10 μm from residual common sensitizing protein component which comprises mixing the biological antigen containing residual common sensitizing protein in phosphate buffered saline having a pH of from about 6.8 to about 7.6 at a temperature of from about 0° to about 10° C. for from about 48 to about 96 hours.

DETAILED DESCRIPTION

This invention is concerned with a process for the isolation of biological materials in an essentially pure state. In particular it is concerned with the isolation of particulate biological materials, with a particle size greater than about 10 nm from growth medium components. Even more particularly it is concerned with isolation of immunizing antigen free of sensitizing plasma protein.

Vaccine technology has been known for many years. The preparation of vaccines against infectious agents frequently includes incubation of an infectious agent in a whole organism animal origin cellular tissue, plasma components and so on. All or most of these growth medium components must be removed from the harvested microorganisms before a completely satisfactory parenteral vaccine can be achieved. This problem of concentration and purification is probably the major impediment to the successful development of commercial vaccine products, once the etiological agents have been isolated, identified and successfully cultivated.

Various techniques have been employed to effect the concentration and purification with varying degrees of success. They fall into three main categories: (1) sedimentation, e.g., centrifugation; (2) adsorption-desorption, e.g., on barium sulfate particles, or on ion exchange resins; and (3) filtration. Each of these processes is primarily a batch operation, and not very efficient so that the unit operation must be repeated many times to approach the state of purity required of a parenteral vaccine. Repetition of unit operations, particularly on a commercial scale, is not only costly from a labor point of view but when dealing with biological products the possibility of contamination is greatly increases and the ensuing losses also can be very costly. The techniques indicated above have distinct shortcomings which are manifested by high costs and inefficiencies.

The prior art has revealed equipment and techniques for the concentration, separation and purification of colloids and macromolecules, such as virus particles, by ultrafiltration with Diaflo$^R$ membranes (Publication No. 415 of Amicon Corporation, Lexington, Mass.). However, the porosity of these membranes made them unsuitable for use with biological particles of larger size such as 10 nm to about 10 μm for example, PPLO, Australia antigen, trachoma agent and the like. Following the teachings of the prior art, one invariably would obtain a conglomeration on the filter membrane of both the desired particulate matter and a variety of various contaminants normally present in crude biological fluid. Particularly undesirable contaminants are residual common sensitizing plasma proteins associated with antigens. Utilizing the prior art technology, a large amount of time, effort and expense would be required to sufficiently purify the resulting conglomerate in order that an essentially pure material is obtained which can be safely and effectively employed as the component of or in the manufacture of vaccines.

Consequently, there is a distinct need for a technique applicable to larger biological particles which would, in effect, be equivalent to repetitive purification-concentration steps but automatic in nature and in a closed system, so that handling, manipulation, and exposure to contamination would be minimized. It was further requirement that the particulate matter resulting from said technique be of sufficient purity to permit its use as components of or in the manufacture of vaccines.

The present invention provides a closed system (for sterility) for the preparation of antigen free from common sensitizing agents such as those present in calf serum. The antigens which with the present invention is concerned are those which are grown in the presence of calf or horse serum, or the like, such serum being an essential nutrient for the desired organism. Such antigens are, e.g., PPLO, and trachoma agent.

As a consequence of being grown in calf or horse serum or the like, the antigen is associated with residual plasma proteins. These residual plasma proteins can sensitize susceptible individuals in whom the antigen is injected. A subsequent injection to a sensitized individual of the same antigen or even more hazardly, of a totally different antigen but containing common sensitizing residual plasma proteins can cause anaphylaxis, which if severe, can result in death.

The process of this invention is one in which the concentration and purification of the desired biological materials, of diameters of from about 10 nm to about 10 μm is carried out in closed, sterile units which are readily scaled up to production size equipment. It results in greater facility for handling of the product with a corresponding decrease in loss of product due to contamination, and a degree of purity heretobefore unavailable from techniques available to the manufacturer of vaccines. In distinct contrast with the prior art, the biological particulate matter prepared in accordance with the instant invention possess sufficient purity and sophistication and freedom from sensitizing plasma proteins to be employed as components of or in the manufacture of vaccines for animals or man.

The process of this invention comprises agitating the biological fluids at lowered temperatures in phosphate buffered saline having a pH of from about 6.8 to about 7.6 to dissociate the residual plasma proteins associated with the antigen. The agitation is continued for from about 24 hours to about 96 hours, at a temperature of from about 0° C to about 10° C, preferably at about 5°C. After the agitation is completed, the partially purified fluids are introduced under pressure to an enclosed filter chamber with a filter of controlled porosity of about 0.22 μ to 0.65 μ with means for maintaining the filter surface essentially free of solids accumulation, means for discharging the filtrate and preferably a means for recycling the retenate through the reservoir of feed material. After the desired concentration of material in the retentate is achieved, the purification is accomplished by adding wash solution to the reservoir at approximately the same rate that filtrate is discharged, until the desired degree of purity is achieved. Alternatively, the concentration material can be diluted with wash fluids and reconcentration a sufficient number of times to achieve the desired purity. The wash cycle is frequently, but not necessarily, performed with a filter of finer porosity than that employed in the concentration phase.

Various means can be employed for keeping the filter surface free from solids accumulation such as stirring, vibrating, scraping or preferably by thin channel filtration. The filtration is conducted at pressures of about 20-60 pounds per square inch, and where employed, the retentate recycle rate is about 2 to 5 liters per minute. Depending on the impurity of the feed material and the particle size of the desired product, an optimum ratio of feed volume to filter surface area is determinable for each concentration-purification operation but has been found to be generally in the range of about 2 to 20 liters of feed per square foot of filter area.

The following examples serve to illustrate the process of the present invention by describing the concentration and purification of certain biological materials. However, the invention is not limited to the specific materials illustrated but is useful in the isolation of any particulate biological matter with a particle size within the described range such as, for example 1. Pleuropneumonia like organisms, e.g., Eaton agent (Mycoplasma pneumoniae;
2. Tric agents, e.g., Trachoma, Psi;
3. Rickettsiae, e.g. R. rickettsi;
4. Virus, e.g., measles, rubella; and
5. Bacteria, e.g. V. cholera

EXAMPLE 1

CONCENTRATION AND PURIFICATION OF PPLO EATON AGENT BY THIN CHANNEL ULTRAFILTRATION

STEP A: PREPARATION OF CRUDE PPLO BROTH

To 1075 ml of calf serum at 5° C. (which had previously been heat treated) there is added gradually with stirring 299 gms (278 mg/ml) of ammonium sulfate.

After 5 minutes stirring, the pH is adjusted with 10N HCl to 6.8. The suspension is stirred at 5° C for 4 hours then centrifuged in a No. 19 rotor at 11,000 rpm (10 minutes). The supernates are decanted and pooled. The pool is dialyzed in 4 bags (27 × 1 inch flat) for 24 hours against running tap water, then for 16 hours at 5° C against phosphate buffered saline, consisting of 7 gms NaCl, 1.7 gms NaHPO$_4$.12H$_2$O, 0.2 gms NaH$_2$PO$_4$.H$_2$O per liter of water. The contents of the dialysis bags are pooled, the final volume being about 1600 ml. This pool is then filtered through a 142 mm diameter pre-filter-0.45 μ Millipore$^R$ combination.

The culture having the following composition is prepared:

| | |
|---|---|
| Difco PPLO broth | 70.0 ml |
| Yeast extract, 25% w/v aqueous | 10.0 ml |
| Fractionated calf serum | 20.0 ml |
| NaHCO$_3$, 7.5% w/v aqueous | 4.0 ml |
| Glucose, 50.0% w/v aqueous | 2.0 ml |

By submerged culture techniques PPLO is cultivated in this medium at 36° C for 4 days.

STEP B: INITIAL CONCENTRATION

Ten liters of PPLO broth from Step A are concentrated and partially purified by processing the fluids through a continuous flow ultracentrifuge rotor (Beckman B-XVI) operating at 35,000 rpms. The fluids are processed at a flow rate of 10 L/hour. The rotor contains a sucrose gradient of 0 to 60% sucrose in phosphate buffered saline. The PPLO product is collected from the sucrose gradient in the density region of 1.16 – 1.20. The PPLO product is then assayed to determine the content of DNA and is subsequently diluted to a DNA level of 30–40 μgs/ml with phosphate buffered saline (pH 7.2).

STEP C: DISSOCIATION

The diluted PPLO sucrose product from Step B is mixed with a magnetic bar rotating at 100–200 rpms for 72 hours at 5° C.

STEP D: FINAL PURIFICATION AND CONCENTRATION

The product from Step C is transferred aseptically to thin channel ultrafiltration equipment which is set up with a 0.22 μm membrane. The PPLO fluids are initially concentrated 10-fold at which time the system is switched to a rinse cycle (diafiltration). The rinse volume used is ten times the volume of the PPLO fluid. The rinse fluid is phosphate buffered saline (pH 7.2).

The final product recovered after this step is purified PPLO articles. The preparation at this point has no detectable serum components when tested in animals.

EXAMPLE 2

CONCENTRATION AND PURIFICATION OF TRACHOMA AGENT

STEP A: GROWTH AND CLARIFICATION

Trachoma agent is grown in the yolk sac membrane of fertilized hen's eggs and harvested in the usual manner. The harvested fluids are clarified by centrifugation at 12,000 X g.

STEP B: CONCENTRATION

One liter of clarified fluids from Step A are processed in a K-II ultracentrifuge using the K-V rotor. The rotor is filled with a sodium bromide step gradient 20 – 27½% – 35% NaBr.

After 3 hours at 30,000 rpms the rate zonal banding is stopped and the product is collected from the density region 1.27 – 1.32. The product is then assayed for content of DNA and is subsequently diluted to a DNA level of 30–40 μgs/ml with phosphate buffered saline (pH 7.2).

STEP C: DISSOCIATION

The Tric agent from Step b is mixed by a magnetic bar at 100–200 rpms for 72 hours at 5° C.

STEP D: FINAL PURIFICATION AND CONCENTRATION

The product from Step C is transferred aseptically to thin channel ultrafiltration equipment which is set up with a 0.22 μm membrane. The Tric fluids are initially rinsed with phosphate buffered saline (pH 7.2) and then concentrated ten-fold. The concentration Tric agent is now rinsed with a 10-fold volume of phosphate buffered saline (pH 7.2).

The preparation at this point is essentially free of contaminating egg protein.

What is claimed is:

1. A process for separating biological immunizing antigen having a particle size of from about 10 nm to about 10 μm from serum derived residual common sensitizing protein components which comprises agitating the biological antigen containing residual common sensitizing protein in phosphate buffered saline having a pH of from about 6.8 to about 7.6 at a temperature of from about 0° C to about 10° C. for from about 48 to about 96 hours.

2. A process according to claim 1 followed by removal of the dissociated residual common sensitizing components from the antigen by mechanical removal in a closed system.

3. A process according to claim 2 wherein the mechanical removal is thin channel ultrafiltration.

4. The process of claim 1, wherein the agitating takes place at a temperature of about 5° C.

5. The process of claim 1, wherein the agitating is carried out for about 72 hours.

6. The process of claim 1, wherein the biological immunizing antigen is PPLO.

7. The process of claim 1, wherein the biological immunizing antigen is Trachoma agent.

8. The process of claim 6, wherein the agitating takes place at about 5° C for about 72 hours.

9. The process of claim 7, wherein the agitating takes place at about 5° C for about 72 hours.

* * * * *